US012702148B2

(12) United States Patent
Ogata et al.

(10) Patent No.: US 12,702,148 B2
(45) Date of Patent: Aug. 11, 2026

(54) ACETYLCHOLINESTERASE INHIBITOR

(71) Applicant: Taiko Pharmaceutical Co., Ltd., Suita (JP)

(72) Inventors: Norio Ogata, Suita (JP); Hideaki Tagishi, Suita (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 999 days.

(21) Appl. No.: 17/442,203

(22) PCT Filed: Sep. 17, 2019

(86) PCT No.: PCT/JP2019/036352
§ 371 (c)(1),
(2) Date: Sep. 23, 2021

(87) PCT Pub. No.: WO2020/202601
PCT Pub. Date: Oct. 8, 2020

(65) Prior Publication Data

US 2022/0183339 A1 Jun. 16, 2022

(30) Foreign Application Priority Data

Mar. 29, 2019 (JP) ................................ 2019-066657

(51) Int. Cl.
*A23L 33/105* (2016.01)
*A61K 31/05* (2006.01)
(Continued)

(52) U.S. Cl.
CPC ............ *A23L 33/105* (2016.08); *A61K 31/05* (2013.01); *A61K 31/085* (2013.01); *A61K 36/15* (2013.01);
(Continued)

(58) Field of Classification Search
CPC ..... A23L 33/105; A61K 31/05; A61K 31/085; A61K 36/15; A61K 36/20; A61K 36/49;
(Continued)

(56) References Cited

U.S. PATENT DOCUMENTS 4,608,258 A * 8/1986 Yamanaka ............ A61K 31/05 424/725.1
5,112,872 A * 5/1992 Baba ...................... A61P 13/02 514/73
(Continued)

FOREIGN PATENT DOCUMENTS

CN 1171237 A 1/1998
CN 101152311 A 4/2008
(Continued)

OTHER PUBLICATIONS

Sierogan; www.seirogan.co.jp/en/products/seirogan/; archived via Wayback Machine on Apr. 26, 2015 (Year: 2015).*
(Continued)

*Primary Examiner* — Jennifer A Berrios
*Assistant Examiner* — Sophia Reilly
(74) *Attorney, Agent, or Firm* — Myers Bigel, P.A.

(57) ABSTRACT

The object of the present invention is to search for and to provide a novel acetylcholinesterase inhibitor. An acetylcholinesterase inhibitor comprising wood creosote as the active ingredient is provided.

6 Claims, 1 Drawing Sheet

(51) Int. Cl.

| | |
|---|---|
| ***A61K 31/085*** | (2006.01) |
| ***A61K 36/15*** | (2006.01) |
| ***A61K 36/20*** | (2006.01) |
| ***A61K 36/49*** | (2006.01) |
| ***A61P 1/00*** | (2006.01) |
| ***A61P 13/02*** | (2006.01) |
| ***A61P 21/04*** | (2006.01) |
| ***A61P 25/16*** | (2006.01) |
| ***A61P 25/18*** | (2006.01) |
| ***A61P 25/28*** | (2006.01) |
| ***A61P 25/30*** | (2006.01) |
| ***A61P 27/06*** | (2006.01) |
| ***A61P 43/00*** | (2006.01) |

(52) U.S. Cl.
CPC .............. *A61K 36/20* (2013.01); *A61K 36/49* (2013.01); *A61P 1/00* (2018.01); *A61P 13/02* (2018.01); *A61P 21/04* (2018.01); *A61P 25/16* (2018.01); *A61P 25/18* (2018.01); *A61P 25/28* (2018.01); *A61P 25/30* (2018.01); *A61P 27/06* (2018.01); *A61P 43/00* (2018.01)

(58) Field of Classification Search
CPC .. A61P 1/00; A61P 13/02; A61P 21/04; A61P 25/16; A61P 25/18; A61P 25/28; A61P 25/30; A61P 27/06; A61P 43/00; A61P 21/00; A61P 25/00
See application file for complete search history.

(56) References Cited

U.S. PATENT DOCUMENTS

| | | | | |
|---|---|---|---|---|
| 6,117,913 | A | 9/2000 | Shibata et al. | |
| 2004/0266659 | A1* | 12/2004 | LaBerge .............. | A61K 31/435 514/214.03 |

FOREIGN PATENT DOCUMENTS

| | | | |
|---|---|---|---|
| JP | 2001335408 | A | 12/2001 |
| JP | 2004166701 | A | 6/2004 |
| JP | 2006315996 | A | 11/2006 |
| JP | 2016204274 | A | 12/2016 |
| WO | 2008099912 | A1 | 8/2008 |

OTHER PUBLICATIONS

Kuge et. al. "Multicenter, Double-Blind, Randomized Comparison of Wood Creosote, the Principal Active Ingredient of Seirogan, an Herbal Antidiarrheal Medication, and Loperamide in Adults with Acute nonspecific Diarrhea" Clinical Therapeutics, Oct. 26, 2004, 1644-1651 (Year: 2004).*

Madisch et. al. "The diagnosis and treatment of functional dyspepsia" Dtsch Arztebl Int 2018, 115, 222-232 (Year: 2018).*

Remington's Pharmaceutical Sciences (17th Ed.) Easton, PA: Mack Publishing Company, 1985 (Year: 1985).*

Acetylcholine Wikipedia Wayback Machine Web Archive Feb. 24, 2018 https://web.archive.org/web/20180224202335/https://en.wikipedia.org/wiki/Acetylcholine (Year: 2018).*

Marucci et. al. "Efficacy of acetylcholinesterase inhibitors in Alzheimer's disease" Neuropharmacology, 2021, 190, 108352, 1-15 (Year: 2021).*

Seirogan Herbal Dietary Supplement Wayback Machine Web Archive Mar. 7, 2018 https://web.archive.org/web/20180307023348/http://seiroganusa.com/ (Year: 2018).*

Seirogan (CAS 852395-11-0) CAS Registry File Accessed Nov. 26, 2024 from STN, entered unto STN Jun. 16, 2005 (Year: 2005).*

Yasri et. al. "Myasthenia gravis exacerbation and diarrhea associated with erythromycin treatment" Journal of Acute Diseases Jun. 2, 2017, 85-86 (Year: 2016).*

Dolhun, et. al. "Dystonia and Parkinson's Disease" Practical Neurology, 2015, 43-46. (Year: 2015).*

Harvey et. al. "The Pharmacology of Galanthamine and Its Analogues" Pharmac. Ther. 1995, 68, 1, 113-128. DOI: 10.1016/0163-7258(95)02002-0 (Year: 1995).*

Ogata et al. "Analysis of beechwood creosote by gas chromatography-mass spectrometry and high-performance liquid chromatography" Research Communications in Chemical Pathology and Pharmacology, 66(3):411-423 (1989).

English translation of International Search Report corresponding to International Patent Application No. PCT/JP2019/036352 (5 pages) (mailed Oct. 21, 2019).

Wang et al. "Toxicity and possible mechanisms of action of honokiol from Magnolia denudata seeds against four mosquito species" Scientific Reports, 9(411):1-19 (2019).

"Acetylcholinesterase inhibitor", Wikipedia, retrieved from https://en.wikipedia.org/wiki/Acetylcholinesterase_inhibitor on Mar. 3, 2025 (13 pages).

"Galantamine", Wikipedia, retrieved from https://en.wikipedia.org/wiki/Galantamine on Mar. 3, 2025 (13 pages).

Ogata, et al., "Inhibition of Acetylcholinesterase by Wood Creosote and Simple Phenolic Compounds", Chem. Pharm. Bull. 68: 1193-1200, 2020.

* cited by examiner

[Figure 1]
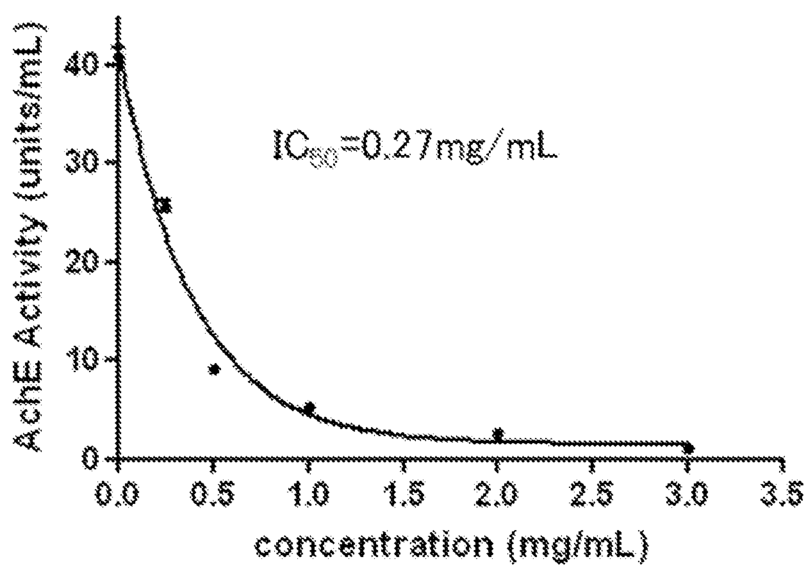
[Figure 2]
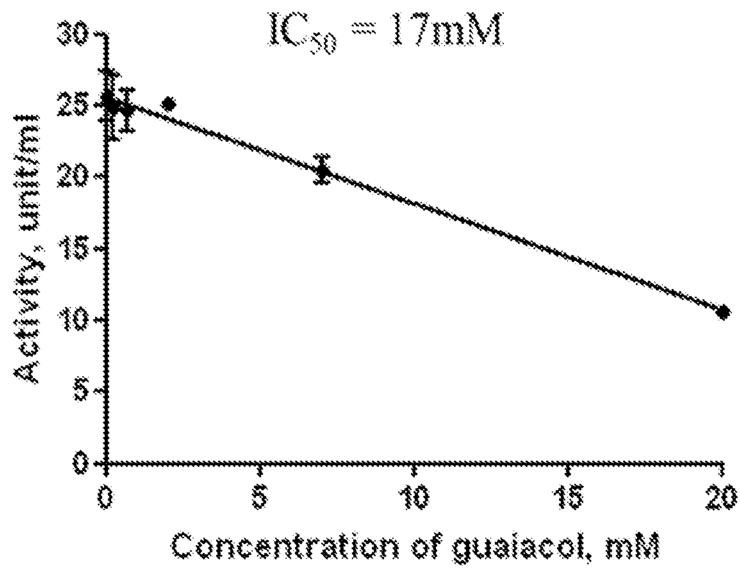

ACETYLCHOLINESTERASE INHIBITOR

TECHNICAL FIELD

The present invention relates to an acetylcholinesterase inhibitor comprising wood creosote, as well as various uses thereof.

BACKGROUND ART

Acetylcholine is a neurotransmitter that is released from the endings of parasympathetic nerves or motor neurons and transmits nerve stimulation. Acetylcholine is retained at a constant concentration in the body by being synthesized by choline acetyltransferase (ChAT) and being degradated by acetylcholinesterase (AChE).

When acetylcholine concentration declines locally in the body, transmission of the cholinergic nerve becomes insufficient. For example, such a state in the brain is thought to be one of the causes of decline in the learning function or the onset of Alzheimer's dementia. Donepezil (product name Aricept) which is a cholinesterase inhibitor is employed as a therapeutic drug for Alzheimer's dementia.

In addition, for example, distigmine bromide is used as a therapeutic purpose for urination disorder, distigmine bromide or ambenonium chloride for myasthenia gravis, and neostigmine or edrophonium as antagonistic drugs for muscle relaxant drugs during general anesthesia. All of these are drugs which aim for the effect of improving pathology by increasing the acetylcholine concentration at the nerve ending with acetylcholinesterase inhibitory action.

However, gastrointestinal symptoms such as vomiting, retching, and diarrhea are pointed out as side effects common to these acetylcholinesterase inhibitors, and a search for drugs with less side effects is in progress (e.g. Patent Literature 1).

CITATION LIST

[Patent Literature 1] Japanese Published Unexamined Patent Application Publication No. 2016-204274

SUMMARY OF THE INVENTION

Problems to be Solved by the Invention

The object of the present invention is to search for and to provide a novel acetylcholinesterase inhibitor.

Means for Solving the Problems

As a result of repeated extensive investigation by the present inventors, it was surprisingly found that wood creosote which is known for an effect as an antidiarrheal drug has acetylcholinesterase inhibitory action, thus coming to complete the present invention.

In other words, the present invention relates to an acetylcholinesterase inhibitor comprising wood creosote as the active ingredient.

One embodiment of the present invention is characterized in that it is a pharmaceutical composition or a food composition comprising acetylcholinesterase inhibitor comprising wood creosote as the active ingredient.

One embodiment of the present invention is characterized in that it is a composition for oral administration or for intrarectal administration, and is prepared so that the dosage of the active ingredient wood creosote will be 0.1-500 mg per 1 kg of body weight per day.

One embodiment of the present invention is characterized in that it is a composition for parenteral administration, and is prepared so that the dosage of the active ingredient wood creosote will be 0.2-300 mg per 1 kg of body weight per day.

Another embodiment of the present invention relates to a pharmaceutical composition or a food composition for treating, improving, or suppressing the progression of a disease or a condition related to a decline in acetylcholine activity.

Another embodiment of the present invention relates to a pharmaceutical composition or a food composition comprising wood creosote as the active ingredient for treating or suppressing the progression of myasthenia gravis.

Another embodiment of the present invention relates to a pharmaceutical composition or a food composition comprising wood creosote as the active ingredient for treating or suppressing the progression of glaucoma.

Another embodiment of the present invention relates to a pharmaceutical composition or a food composition comprising wood creosote as the active ingredient for treating or suppressing the progression of Alzheimer-type dementia.

Another embodiment of the present invention relates to a pharmaceutical composition or a food composition comprising wood creosote as the active ingredient for treating or suppressing the progression of Lewy body-type dementia.

Another embodiment of the present invention relates to a pharmaceutical composition or a food composition comprising wood creosote as the active ingredient for treating or suppressing the progression of Parkinson's syndrome.

Another embodiment of the present invention relates to a pharmaceutical composition or a food composition comprising wood creosote as the active ingredient for treating or suppressing the progression of dysuria.

Another embodiment of the present invention relates to a pharmaceutical composition or a food composition comprising wood creosote as the active ingredient for treating or suppressing the progression of dyschezia.

Another embodiment of the present invention relates to a pharmaceutical composition or a food composition comprising wood creosote as the active ingredient for treating or suppressing the progression of functional dyspepsia.

Another embodiment of the present invention relates to a pharmaceutical composition or a food composition comprising wood creosote as the active ingredient for detoxifying anticholinergic drug poisoning.

Another embodiment of the present invention relates to a pharmaceutical composition or a food composition comprising wood creosote as the active ingredient for suppressing nondepolarizing muscle relaxant drugs (removing residual muscle relaxant action).

Another embodiment of the present invention relates to a pharmaceutical composition or a food composition comprising wood creosote as the active ingredient for increasing incidents of lucid dream (increasing the proportion of REM sleep).

Another embodiment of the present invention relates to a pharmaceutical composition or a food composition comprising wood creosote as the active ingredient for treating cognitive disorder of schizophrenic patients.

Another embodiment of the present invention relates to an herbicide comprising wood creosote as the active ingredient.

Another embodiment of the present invention relates to an insecticide comprising wood creosote as the active ingredient (insecticide for insects or nematodes).

Another embodiment of the present invention relates to the use of wood creosote in manufacturing a pharmaceutical for treating, improving, or suppressing the progression of a disease or a condition related to a decline in acetylcholine activity.

Another embodiment of the present invention relates to a therapeutic method or a method for suppression of progression of a disease or a condition related to a decline in acetylcholine activity in a subject comprising:

a step of applying an effective amount of wood creosote to said subject.

One embodiment of the present invention is characterized in that said disease or a condition related to a decline in acetylcholine activity is one or more diseases or conditions selected from the group consisting of:

myasthenia gravis,
glaucoma,
Alzheimer-type dementia,
Lewy body-type dementia,
Parkinson's syndrome,
dysuria,
dyschezia,
functional dyspepsia,
anticholinergic drug poisoning,
residual muscle relaxation due to a nondepolarizing muscle relaxant drug,
reduced incidents of lucid dream, and
cognitive disorder of schizophrenic patients.

One embodiment of the present invention is characterized in that application of wood creosote to a subject is oral administration or intrarectal administration, and the dosage of wood creosote is 0.1-500 mg per 1 kg of body weight per day.

One embodiment of the present invention is characterized in that application of wood creosote to said subject is parenteral administration, and the dosage of wood creosote is 0.2-300 mg per 1 kg of body weight per day.

An invention of any combination of one or more characteristics of the present invention listed above is also encompassed by the scope of the present invention.

Effects of the Invention

The acetylcholinesterase inhibitor of the present invention not only has a drug effect based on acetylcholinesterase inhibitory activity, but may also reduce side effects (gastrointestinal symptoms) of preexisting acetylcholinesterase inhibitors due to the antidiarrheic action of wood creosote.

BRIEF DESCRIPTION OF THE DRAWINGS

FIG. 1 shows a graph plotting the acetylcholinesterase inhibitory activity of wood creosote at each concentration.

FIG. 2 shows a graph plotting the acetylcholinesterase inhibitory activity of guaiacol at each concentration.

DESCRIPTION OF EMBODIMENTS

The present invention relates to an acetylcholinesterase inhibitor comprising wood creosote as the active ingredient, as well as various uses thereof.

Wood Creosote

The active ingredient wood creosote of the present invention itself is conventionally well-known, and is listed in the Pharmacopeia of Japan, the National Formulary of the U.S.A., and the like. The active ingredient wood creosote of the present invention is so-called wood creosote which is obtained by distilling wood tar obtained from trees, in particular broad-leaved trees such as beech, oak, maple, and pine, and collecting the fraction at approximately 200-230° C. (760 mmHg) by fractional distillation. Wood creosote is clearly distinguished from creosote obtained from coal tar (N. Ogata and T. Baba, Res. Commun. Chem. Pathol. Pharmacol. 66, 411-423, 1989)).

The active ingredient wood creosote of the present invention is a clear to light yellow-colored solution comprising guaiacol, creosol, phenol, p-cresol, 4-ethylguaiacol, o-cresol, and the like.

Formulations (Forms)

In the present invention, the above wood creosote is used in the form of general pharmaceutical compositions (such as medical agents) or food compositions (such as supplements). In other words, it is prepared according to conventional means employing pharmaceutically accepted ordinarily used excipients or diluents, and can be in various forms depending on the therapeutic purpose. Representatives thereof include, for example, dosage forms suitable for oral administration such as tablets, pills, powders, capsules, soft capsules, granules, and oral liquids, dosage forms suitable for intravascular administration, intramuscular administration, subcutaneous or intracutaneous administration, and the like, such as injections, as well as dosage forms suitable for intrarectal administration such as suppositories.

When preparing in the form of tablets, granules, and powders, well-known supports can be broadly used, and e.g. excipients such as lactose, white sugar, glucose, starch, and crystal cellulose, e.g. binders such as hydroxypropylcellulose, methylcellulose, gelatin, tragacanth, gum arabic, and sodium alginate, e.g. disintegrants such as starch, carboxymethylcellulose, and calcium carbonate, as well as e.g. lubricants such as magnesium stearate, talc, and stearic acid can be used. For tablets, ordinary coatings can also be applied as necessary to make e.g. sugar-coated tablets, film-coated tablets, and the like, and these may further be bilayer tablets or multilayer tablets. Moreover, ordinary coatings may also be applied to granules or powders.

Various supports conventionally well-known in the field can also be employed when preparing in the form of pills, and e.g. excipients such as licorice powder, glucose, and wheat flour, e.g. binders such as glycerin, water syrup, gum arabic, tragacanth, and gelatin, as well as disintegrants such as medicinal yeast, arrowroot, and laminaria powder can be used.

In order to prepare in the form of capsules, various supports conventionally well-known in the field, e.g. excipients such as lactose, olive oil, and soybean oil can be used.

Liquids for internal use may be water-based or oil-based suspensions, solutions, syrups, or other forms. For such liquid formulations, commonly employed additives, for example suspending agents, e.g. sorbit syrup, methylcellulose, gelatin, and carboxymethylcellulose, as well as emulsifiers, e.g. lecithin, sorbitan monoolefinate, gum arabic, and the like can be used.

In order to prepare in the form of injections, the composition may be in a form such as suspensions, solutions, or emulsions in oil-based or water-based vehicles, or the composition may comprise formulating agents such as suspending agents, stabilizers, and dispersants.

In order to prepare in the form of suppositories, well-known supports can be broadly used. For example, bases such as cacao butter, glycerogelatin, and macrogol can be used. For suppositories, emulsifiers and suspending agents can be used as necessary. Further, coloring agents, flavoring agents, and the like can also be added to the agent of the present invention as necessary.

The amount of wood creosote contained in the pharmaceutical composition or the food composition of the present invention as the active ingredient is not particularly limited and may be appropriately selected depending on the form of the formulation and the like, and is in general preferably approximately 0.2-60% of the total weight of the formulation.

The dosage of the pharmaceutical composition or the food composition of the present invention is appropriately selected according to the sex, age, weight, the extent of symptoms, and the like of the patient, and in adults, may be in general, for oral administration and intrarectal administration, approximately 0.1-500 mg, preferably approximately 2-100 mg, and more preferably approximately 2-25 mg of the active ingredient wood creosote for 1 kg of body weight per day. When parenterally administered as injections, similarly in adults, the dosage may be approximately 0.2-300 mg, preferably approximately 0.2-50 mg, and more preferably approximately 0.5-5 mg of the active ingredient wood creosote for 1 kg of body weight per day. Note that these may be administered divided into approximately 2-4 times per day.

Specific Uses

The acetylcholinesterase inhibitor of the present invention may be utilized for additional various specific uses. For example, the acetylcholinesterase inhibitor of the present invention can be employed for treating myasthenia gravis, glaucoma, Alzheimer-type dementia, Lewy body-type dementia, Parkinson's syndrome, urination/dyschezia, functional dyspepsia, and the like, where therapeutic effects by other acetylcholinesterase inhibitors have already been confirmed. Moreover, the acetylcholinesterase inhibitor of the present invention can also be employed for detoxifying anticholinergic drug poisoning, suppressing nondepolarizing muscle relaxant drugs, increasing incidents of lucid dream, treating cognitive disorder of schizophrenic patients, and the like. Further, the acetylcholinesterase inhibitor of the present invention, due to its action mechanism, can also be employed as herbicides or insecticides (such as insecticides for expelling insects).

The terms used herein are employed for describing particular embodiments, and do not intend to limit the invention.

Moreover, the term "comprising" as used herein, unless the content clearly indicates to be understood otherwise, intends the presence of the described items (such as components, steps, elements, or numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, should be construed as having meanings consistent with the meanings herein and in related technical fields, and shall not be construed as having idealized or excessively formal meanings.

The embodiments of the present invention may be described with reference to schematic diagrams. In such a case, they may be exaggerated in presentation in order to allow clear description.

As used herein, for example when expressed as "1-10 w/w %," those skilled in the art will recognized that said expression individually and specifically refers to 1, 2, 3, 4, 5, 6, 7, 8, 9, or 10 w/w %.

As used herein, any and all numeric values employed to indicate component contents or numeric value ranges are, unless explicitly indicated, construed to encompass the meaning of the term "about." For example, "10-fold," unless explicitly indicated, is recognized to mean "about 10-fold."

All of the disclosures of the literatures cited herein should be deemed as cited herein, and those skilled in the art will cite and recognize the related disclosed contents in these prior art literatures as a part of the present specification according to the context herein without departing from the spirit and scope of the present invention.

EXAMPLES

Example 1: Measurement of Acetylcholinesterase Activity of Wood Creosote

<Experimental Materials>

1. Test Substances 1.1 Test Substance 1

Name: Wood creosote (hereinafter described as WC)

Molecular weight: No molecular weight shown since this is a mixture

Obtained from: Taiko Pharmaceutical Co., Ltd.

Storage condition: Refrigerated (4° C.), protected from light 1.2 Test Substance 2 (positive control)

Name: Galantamine hydrobromide salt (hereinafter described as GAL)

Molecular weight: 368.3

Serial number: G1660-2 MG

Obtained from: Sigma-Aldrich

Storage condition: Frozen (−20° C.)

*Galantamine is known as a substance having acetylcholinesterase inhibitory action, and is employed for treating light to moderate Alzheimer-type dementia or memory disorder.

2. Reagents 2.1 AchE Enzyme

Name: Acetylcholinesterase from *Electrophorus electricus* (electric eel) Type VI-S Serial number: C3389-500UN Obtained from: Sigma-Aldrich Storage condition: Frozen (−20° C.)

2.2 AchE Activity Measurement Kit

Name: Acetylcholinesterase Activity Assay Kit

Serial number: MAK119

Obtained from: Sigma-Aldrich

Storage condition: Room temperature 2.3 Solvent

Name: UltraPure 1M Tris-HCL pH 7.5

Serial number: 15567-027

Obtained from: Invitrogen

Storage condition: Refrigerated (4° C.)

2.4 Water

Water purified with ultrapure water production device UL-Pure was used (hereinafter shortened to ultrapure water.)

3. Instruments/Appliances Used 3.1 Electronic Balance

Model: AUX120

Manufacturer: SHIMADZU 3.2 Pipette

Model: Pipetman P series

Manufacturer: GILSON 3.2 Continuous Dispenser (multichannel pipette)

Model: Pipetman Neo series

Manufacturer: GILSON 3.3 Thermobath
Model: BF400
Manufacturer: Yamato Scientific
3.4 Refrigerator-Freezer
Model: GR-38ND
Manufacturer: TOSHIBA
3.5 Microplate Reader
Model: SH-9000Lab
Manufacturer: CORONA ELECTRIC
3.6 96-Well Microplate
Model: 353072
Manufacturer: FALCON <Test Method>

1. Preparation of Test Substance 1 Solution

WC was weighed and dissolved in ultrapure water to prepare to a concentration of 5 mg/mL, and test substance 1 solution was obtained.

2. Preparation of Test Substance 2 Solution

GAL was weighed and dissolved in ultrapure water to a concentration of 1 mg/mL. This was then further diluted 1.25-folds with ultrapure water to prepare to a concentration of 800 μg/mL, and test substance 2 solution was obtained.

3. Preparation of AchE Enzyme Solution

AchE enzyme (lyophilized powder) 2 mg (500 units) was dissolved in 2 mL of Tris-HCL Buffer pH 7.5 prepared to a concentration of 20 mM. This was then further diluted 30-folds with ultrapure water to prepare to a concentration of 33.3 μg/mL.

4. Preparation of Working Solution for Measuring AchE Activity

Two mg of the reagent included in the AchE activity measurement kit was weighed, dissolved in 200 mL of the assay buffer, and the working solution was obtained.

5. Measurement Procedure 5.1 Measurement of AchE Activity of Test Substance 1 (WC)

Measurement was carried out according to the following order.

1) AchE enzyme solution (33.3 μg/mL) is mixed with test substance 1 solution (5 mg/mL) and ultrapure water according to the following Table 1.

TABLE 1

| Composition of the reaction solution | | | | | | |
|---|---|---|---|---|---|---|
| Sample | WC1 | WC2 | WC3 | WC4 | WC5 | WC6 |
| AchE enzyme solution (33.3 μg/mL) | 25 μL | 25 μL | 25 μL | 25 μL | 25 μL | 25 μL |
| Test substance 1 solution (5.0 mg/mL) | 0 μL | 5 μL | 10 μL | 20 μL | 40 μL | 60 μL |
| Ultrapure water | 75 μL | 70 μL | 65 μL | 55 μL | 35 μL | 15 μL |
| Total amount | 100 μL | 100 μL | 100 μL | 100 μL | 100 μL | 100 μL |
| WC concentration | 0 mg/mL | 0.25 mg/mL | 0.5 mg/mL | 1.0 mg/mL | 2.0 mg/mL | 3.0 mg/mL |

2) The mixture is allowed to react in a thermobath at 37° C. for 10 minutes.

3) 200 μL each of ultrapure water is added to 4 wells (n=4) of a 96-well microplate (blank wells.)

4) 200 μL each of the calibrator included in the AchE activity measurement kit is added to 4 wells (n=4) different from those in Procedure 3) (calibrator wells.)

5) 190 μL each of the working solution is added to yet another 24 wells (6 samples×4) (sample wells.)

6) To the wells with the working solution added, 10μ each of post-reaction solutions No. 1-6 obtained in Procedure 2) is added to 4 wells (n=4) each.

7) The plates are lightly tapped to allow mixing, reacted for 2 minutes at room temperature, and then absorbance at 412 nm is read with a microplate reader.

8) This is allowed to react for another 8 minutes at room temperature (a total of 10 minutes), and then the absorbance at 412 nm is measured.

5.2 Measurement of AchE Activity of Test Substance 2 (GAL)

Measurement was carried out according to the following order.

1) AchE enzyme solution (33.3 μg/mL) is mixed with test substance 2 solution (800 μg/mL) and ultrapure water according to the following Table 2.

TABLE 2

| Composition of the reaction solution | | | | | | |
|---|---|---|---|---|---|---|
| Sample | GAL1 | GAL2 | GAL3 | GAL4 | GAL5 | GAL6 |
| AchE enzyme solution (33.3 μg/mL) | 25 μL | 25 μL | 25 μL | 25 μL | 25 μL | 25 μL |
| Test substance 2 solution (800 μg/mL) | 0 μL | 5 μL | 10 μL | 20 μL | 40 μL | 60 μL |
| Ultrapure water | 75 μL | 70 μL | 65 μL | 55 μL | 35 μL | 15 μL |
| Total amount | 100 μL | 100 μL | 100 μL | 100 μL | 100 μL | 100 μL |
| GAL concentration | 0 mg/mL | 0.04 mg/mL | 0.08 mg/mL | 0.16 mg/mL | 0.32 mg/mL | 0.48 mg/mL |

2) The mixture is allowed to react in a thermobath at 37° C. for 10 minutes.

3) 200 μL each of ultrapure water is added to 4 wells (n=4) of a 96-well microplate (blank wells.)

4) 200 μL each of the calibrator included in the AchE activity measurement kit is added to 4 wells (n=4) different from those in Procedure 3) (calibrator wells.)

5) 190 μL each of the working solution is added to yet another 24 wells (6 samples×4) (sample wells.)

6) To the wells with the working solution added, 10μ each of post-reaction solutions No. 1-6 obtained in Procedure 2) is added to 4 wells (n=4) each.

7) The plates are lightly tapped to allow mixing, reacted for 2 minutes at room temperature, and then absorbance at 412 nm is read with a microplate reader.

8) This is allowed to react for another 8 minutes at room temperature (a total of 10 minutes), and then the absorbance at 412 nm is measured.

6. Data Processing

Employing the absorbance values obtained, the AchE activity (units/mL) was calculated by the formula below, and the average value and standard deviation of the AchE activity (units/mL) for each test substance at each concentration was calculated.

[Formula 1]

$$AchE\ \text{Activity (units/mL)} = \frac{(A_{412})_{final} - (A_{412})_{initial}}{(A_{412})_{calibrator} - (A_{412})_{blank}} \times n \times 0.2$$

$(A_{412})$ final: Absorbance value at 412 nm after 10 minutes of reaction $(A_{412})$ initial Absorbance value at 412 nm after 2 minutes of reaction n: Dilution coefficient (n=120)

0.2: Coefficient by Calibrator

Moreover, employing the AchE activity for the test substance at each concentration, One phase exponential decay curve was obtained by GraphPad Prism, and the $IC_{50}$ value (mg/mL) was calculated.

<Test Results>

1. Acetylcholinesterase Activity of Wood Creosote (WC)

The average value and standard deviation value of AchE activity (units/mL) of test substance 1 (WC) and test substance 2 (GAL) obtained for each well are indicated below.

TABLE 3

| Average value and standard deviation (WC) of AchE activity (units/mL) (n = 4) | | | | |
|---|---|---|---|---|
| Sample | WC concentration (mg/mL) | AchE activity (units/mL) | Standard deviation | Inhibitory rate (%) |
| WC1 | 0 | 40.91 | 1.66 | 0 |
| WC2 | 0.25 | 25.65 | 1.21 | 37.3 |
| WC3 | 0.50 | 9.249 | 0.524 | 77.4 |
| WC4 | 1.0 | 5.249 | 0.154 | 87.2 |
| WC5 | 2.0 | 2.647 | 0.102 | 93.5 |
| WC6 | 3.0 | 0.9517 | 0.0144 | 97.7 |

TABLE 4

| Average value and standard deviation (GAL) of AchE activity (units/mL) (n = 4) | | | | |
|---|---|---|---|---|
| Sample | GAL concentration (mg/mL) | AchE activity (units/mL) | Standard deviation | Inhibitory rate (%) |
| GAL1 | 0 | 40.22 | 0.908 | 0 |
| GAL2 | 0.04 | 20.10 | 0.520 | 50.0 |
| GAL3 | 0.08 | 12.05 | 0.632 | 70.0 |

TABLE 4-continued

| Average value and standard deviation (GAL) of AchE activity (units/mL) (n = 4) | | | | |
|---|---|---|---|---|
| Sample | GAL concentration (mg/mL) | AchE activity (units/mL) | Standard deviation | Inhibitory rate (%) |
| GAL4 | 0.16 | 7.00 | 0.111 | 83.6 |
| GAL5 | 0.32 | 3.82 | 0.138 | 90.5 |
| GAL6 | 0.48 | 2.90 | 0.138 | 92.8 |

2. Calculation of $IC_{50}$

The nonlinear regression curve obtained employing the AchE activity value at each concentration of test substance 1 obtained, as well as the $IC_{50}$ values are shown in FIG. 1. As shown in FIG. 1, the $IC_{50}$ value was 0.27 mg/mL. Note that since the average molecular weight of components contained in wood creosote is 129, when subjected to unit conversion to mM the $IC_{50}$ value is 2.1 mM.

From the above results, acetylcholinesterase inhibitory action of wood creosote (WC) was confirmed. Moreover, it was shown that wood creosote has acetylcholinesterase inhibitory activity comparable to galantamine (GAL) which is already in actual use as an acetylcholinesterase inhibitor.

Discussion

From the results of this research, it was shown that wood creosote has superior acetylcholinesterase inhibitory action. This result suggests that wood creosote may be employed for treating or improving various diseases or conditions attributed to acetylcholinesterase. Moreover, since wood creosote is a substance which is already in broad use as an antidiarrheal drug, the acetylcholinesterase inhibitor of the present invention is anticipated to reduce gastrointestinal symptoms which is a common side effect of preexisting acetylcholinesterase inhibitors.

Example 2: Comparison of Acetylcholinesterase Activity Between Wood Creosote and Guaiacol <Experimental Materials>

1. Test Substance

Test Substance 3

Name: Guaiacol (hereinafter described as GUA)

Molecular weight: 124.14

Obtained from: Tokyo Chemical Industry Co., Ltd.

Storage condition: Room temperature, protected from light

2. Reagents 2.1 AchE Enzyme

Name: Acetylcholinesterase from *Electrophorus electricus* (electric eel) Type VI-S Serial number: C3389-500UN Obtained from: Sigma-Aldrich Storage condition: Frozen (−20° C.)

2.2 AchE Activity Measurement Kit

Name: Acetylcholinesterase Activity Assay Kit

Serial number: MAK119

Obtained from: Sigma-Aldrich

Storage condition: Room temperature 2.3 Water

Water purified with ultrapure water production device UL-Pure was used (hereinafter shortened to ultrapure water.)

3. Instruments/Appliances Used 3.1 Electronic Balance

Model: AUX120

Manufacturer: SHIMADZU 3.2 Pipette

Model: Pipetman P series

Manufacturer: GILSON 3.2 Continuous Dispenser (multichannel pipette)

Model: Pipetman Neo series

Manufacturer: GILSON 3.3 Thermobath

Model: BF400

Manufacturer: Yamato Scientific 3.4 Refrigerator-Freezer

Model: GR-38ND

Manufacturer: TOSHIBA 3.5 Microplate Reader

Model: SH-9000Lab

Manufacturer: CORONA ELECTRIC 3.6 96-Well Microplate

Model: 353072

Manufacturer: FALCON

<Test Method>

1. Preparation of Test Substance 3 Solution

GUA was weighed and dissolved in ultrapure water to prepare to a concentration of 40 mM, and test substance 3 solution was obtained.

2. Preparation of AchE Enzyme Solution

AchE enzyme (lyophilized powder) 2 mg (500 units) was dissolved in 2 mL of Tris-HCL Buffer pH 7.5 prepared to a concentration of 20 mM. This was then further diluted 30-folds with ultrapure water to prepare to a concentration of 33.3 μg/mL.

3. Preparation of Working Solution for Measuring AchE Activity

Two mg of the reagent included in the AchE activity measurement kit was weighed, dissolved in 200 mL of the assay buffer, and the working solution was obtained.

4. Measurement Procedure 4.1 Measurement of AchE Activity of Test Substance 3

Measurement was carried out according to the following order.

1) AchE enzyme solution (33.3 μg/mL) is mixed with test substance 3 solution (40 mM) and ultrapure water according to the following Table 5.

TABLE 5

| Composition of the reaction solution | | | | | | |
|---|---|---|---|---|---|---|
| Sample | GUA1 | GUA2 | GUA3 | GUA4 | GUA5 | GUA6 |
| AchE enzyme solution (33.3 μg/mL) | 25 μL | 25 μL | 25 μL | 25 μL | 25 μL | 25 μL |
| Ultrapure water | 75 μL | 74.5 μL | 73.3 μL | 70 μL | 57.5 μL | 25 μL |
| Test substance 3 solution (40 mM) | 0 μL | 0.5 μL | 1.75 μL | 5 μL | 17.5 μL | 50 μL |
| Total amount | 100 μL | 100 μL | 100 μL | 100 μL | 100 μL | 100 μL |
| GUA concentration | 0 mM | 0.2 mM | 0.7 mM | 2 mM | 7 mM | 20 mM |

2) The mixture is allowed to react in a thermobath at 37° C. for 10 minutes.
3) 200 μL each of ultrapure water is added to 3 wells (n=3) of a 96-well microplate (blank wells.)
4) 200 μL each of the calibrator included in the AchE activity measurement kit is added to 3 wells (n=3) different from those in Procedure 3) (calibrator wells.)
5) 190 μL each of the working solution is added to yet another 18 wells (6 samples×3) (sample wells.)
6) To the wells with the working solution added, 10μ each of post-reaction solutions No. 1-6 obtained in Procedure 2) is added to 3 wells (n=3) each.
7) The plates are lightly tapped to allow mixing, reacted for 2 minutes at room temperature, and then absorbance at 412 nm is read with a microplate reader.
8) This is allowed to react for another 8 minutes at room temperature (a total of 10 minutes), and then the absorbance at 412 nm is measured.

5. Data Processing

Employing the absorbance values obtained, the AchE activity (units/mL) was calculated by the formula below, and the average value and standard deviation of the AchE activity (units/mL) for each test substance at each concentration was calculated.

$$AchE \text{ Activity (units/mL)} = \frac{(A_{412})_{final} - (A_{412})_{initial}}{(A_{412})_{calibrator} - (A_{412})_{blank}} \times n \times 0.2 \quad \text{[Formula 2]}$$

$(A_{412})$ final: Absorbance value at 412 nm after 10 minutes of reaction
$(A_{412})$ initial Absorbance value at 412 nm after 2 minutes of reaction
n: Dilution coefficient (n=120)
0.2: Coefficient by calibrator Moreover, employing the AchE activity obtained for the test substance at each concentration, the regression curve was obtained by GraphPad Prism, and the $IC_{50}$ value (mM) was calculated.

<Test Results>

1. Test Results of Test Substance 3

The average value and standard deviation value of AchE activity (units/mL) of test substance 3 (GUA) obtained for each well are indicated below.

TABLE 6

| Average value and standard deviation of AchE activity (units/mL) | | | | |
|---|---|---|---|---|
| Sample | GUA concentration (mM) | AchE activity (units/mL) | Standard deviation | Inhibitory rate (%) |
| GUA1 | 0 | 25.65 | 1.74 | 0 |
| GUA2 | 0.2 | 24.89 | 2.24 | 3.0 |
| GUA3 | 0.7 | 24.64 | 1.45 | 3.9 |
| GUA4 | 2 | 25.09 | 0.36 | 2.2 |
| GUA5 | 7 | 20.54 | 0.90 | 19.9 |
| GUA6 | 20 | 10.56 | 0.18 | 58.8 |

2. Calculation of $IC_{50}$

The nonlinear regression curve obtained employing the AchE activity value at each concentration of test substance 3 obtained, as well as the $IC_{50}$ value are shown in FIG. 2. As shown in FIG. 2, the $IC_{50}$ value was 17 mg/mL.

Discussion

In the acetylcholinesterase inhibition test of Example 1, the $IC_{50}$ of wood creosote was 2.1 mM. In Example 2, acetylcholinesterase inhibition test of guaiacol was performed under conditions similar to those in Example 1, and the $IC_{50}$ was 17 mM. In other words, it was shown that wood creosote has about 8 to 9-folds higher acetylcholinesterase inhibitory activity than the single component guaiacol.

The invention claimed is:

1. A method for suppressing progression of a disease or a condition related to a decline in acetylcholine activity in a subject in need thereof, comprising:
applying an effective amount of wood creosote to said subject, thereby suppressing progression of said disease or said condition in said subject;
wherein said disease or said condition is myasthenia gravis.

2. The method according to claim 1, wherein:
applying said effective amount of wood creosote to said subject is via oral administration, and
wherein said effective amount of wood creosote is 0.1-500 mg per 1 kg of body weight of said subject per day.

3. The method according to claim 1, wherein:
applying said effective amount of wood creosote to said subject is via parenteral administration, and
wherein said effective amount of wood creosote is 0.2-300 mg per 1 kg of body weight of said subject per day.

4. The method according to claim 1, wherein applying said effective amount of wood creosote to said subject is via parenteral administration.

5. The method according to claim 1, wherein:
applying said effective amount of wood creosote to said subject is via intrarectal administration, and
wherein said effective amount of wood creosote is 0.1-500 mg per 1 kg of body weight of said subject per day.

6. The method according to claim 1, wherein said effective amount of wood creosote is 0.3-100 mg per 1 kg of body weight per day.

* * * * *